United States Patent [19]
Mainz et al.

[11] Patent Number: 5,113,027
[45] Date of Patent: May 12, 1992

[54] OXYCHLORINATION PROCESS USING A CATALYST WHICH COMPRISES COPPER CHLORIDE SUPPORTED ON RARE-EARTH MODIFIED ALUMINA

[75] Inventors: Eric L. Mainz, Colwich; William Q. Beard, Jr.; Robert P. Hirschmann, both of Wichita, all of Kans.; Barry M. Little, Castlewood, S. Dak.; Earl B. Smith, Newton, Kans.

[73] Assignee: Vulcan Materials Company, Wichita, Kans.

[21] Appl. No.: 533,513

[22] Filed: Jun. 5, 1990

Related U.S. Application Data

[63] Continuation-in-part of Ser. No. 451,303, Dec. 15, 1989.

[51] Int. Cl.$^5$ .................. C07C 17/152; C07C 17/151
[52] U.S. Cl. ...................................... 570/224
[58] Field of Search ......................................... 570/224

[56] References Cited

U.S. PATENT DOCUMENTS

| | | |
|---|---|---|
| 2,636,864 | 4/1953 | Pye et al. |
| 3,210,431 | 10/1965 | Engel |
| 3,267,162 | 8/1966 | Bohl |
| 3,296,319 | 1/1967 | Bohl |
| 3,360,483 | 12/1967 | Diamond et al. |
| 3,624,170 | 11/1971 | Wakiyama et al. |
| 3,634,300 | 1/1972 | Yerres et al. |
| 3,657,367 | 4/1972 | Blake et al. |
| 3,899,444 | 8/1975 | Stephens |
| 4,069,170 | 1/1978 | Blake et al. |
| 4,124,534 | 11/1978 | Leitert et al. |
| 4,158,645 | 6/1979 | Magistro |
| 4,159,968 | 7/1979 | Kroenke et al. |
| 4,414,136 | 11/1983 | Convers |
| 4,446,249 | 5/1984 | Eden |
| 4,463,200 | 7/1984 | Beard, Jr. et al. |
| 4,587,230 | 5/1986 | Cavaterra et al. |
| 4,722,920 | 2/1988 | Kimura et al. |

FOREIGN PATENT DOCUMENTS

| | | |
|---|---|---|
| 701913 | 1/1965 | Canada |
| 1256074 | 12/1971 | United Kingdom |

OTHER PUBLICATIONS

Abstract: CA:72:31207p (1970) corresponds to British Pat. No. 1,256,074.
Abstract: CA 72:31208b (1970) corresponds to German Publ. No. 1,917,041.
Abstract: CA 72:71145y (1970) corresponds to German Publ. No. 1,920,685.
Abstract: CA 78:71395d (1973) corresponds to German Publ. No. 2,226,657.
Abstract: CA 78:75562d (1973) corresponds to German Publ. No. 2,228,452.
Abstract: CA 105:103451 (1986) corresponds to European Publ. No. EP 184,506.
Abstract: CA 83:78548t (1975) corresponds to Spanish Pat. No. 396,465.
Abstract: CA 83:78549u (1975) corresponds to Spanish Pat. No. 496,467.
Abstract: CA 105:103446r (1986) corresponds to JP 6135851 (86 35,851).
Abstract: CA 105:103447s (1986) corresponds to JP 6138627 (85 38,627).
Abstract: CA 98:106780t (1983) corresponds to Braz. PI BR 82 00,180.

*Primary Examiner*—Howard T. Mars
*Attorney, Agent, or Firm*—Burns, Doane, Swecker & Mathis

[57] ABSTRACT

A superior catalyst for the oxychlorination of $C_2$ hydrocarbon feeds comprises a mixture of copper chloride and alkali metal chloride, especially potassium chloride, and preferably also magnesium chloride, which mixture is deposited on an alumina support that has been thermally stabilized by integral incorporation therein of a certain class of lanthanide oxide. The use of such thermally stable catalyst in the production of chlorinated hydrocarbons such as trichloroethylene and perchloroethylene by oxychlorination of a $C_2$ hydrocarbon feed results in particularly good process efficiencies in terms of long on-stream times, relatively low reactor corrosion rates, high HCl conversion, reduced burning, and conveniently flexible selectivity to specifically desired product.

6 Claims, No Drawings

OXYCHLORINATION PROCESS USING A CATALYST WHICH COMPRISES COPPER CHLORIDE SUPPORTED ON RARE-EARTH MODIFIED ALUMINA

BACKGROUND OF THE INVENTION

1. Cross-Reference to Related Application

This application is a continuation-in-part of parent application Ser. No. 07/451,303 filed Dec. 15, 1989. The entire contents of said parent application are hereby incorporated herein by reference.

2. Field of the Invention

The invention relates to the production of perchloroethylene and trichloroethylene by catalytic oxychlorination of $C_2$ hydrocarbons or their partially chlorinated derivatives, to catalyst compositions for use in such oxychlorination processes and to modified alumina supports used in making such catalysts.

3. General Background and Summary of the Prior Art

Perchloroethylene, $C_2Cl_4$, and trichloroethylene, $C_2HCl_3$, are chlorinated hydrocarbons which are widely used as solvents in dry cleaning textiles, in degreasing metal parts, in various solvent extraction processes, in compounding rubber cements, and in various other operations. Because perchloroethylene is relatively stable, its use is much less severely restricted by anti-pollution regulations than is the use of most other chlorinated solvents and is therefore a particularly desirable product. Trichloroethylene is becoming increasingly important as a raw material for the manufacture of replacement refrigerants for fully halogenated refrigerant compounds currently in use.

Both $C_2Cl_4$ and $C_2HCl_3$ have been commonly produced by catalytic oxychlorination of ethane, ethylene or a partially chlorinated derivative thereof, i.e., by reacting such a feedstock with hydrogen chloride or chlorine and air or oxygen at a suitable temperature in the presence of a suitable catalyst which is maintained in the reaction zone either as a fixed bed or, more preferably, as a fluidized bed.

Typically, such catalyst compositions comprise a catalytic amount of a metal having a variable valence, such as copper, as well as an alkali metal, such as potassium, supported on a suitable carrier. Carriers used commercially in the past have included highly calcined fuller's earth, such as "Florex", or preferably synthetic activated aluminas. See, for instance, U.S. Pat. Nos. 3,267,162, 3,296,319 and 4,463,200. Fuller's earth is essentially a magnesium-aluminum silicate containing small proportions of oxides of iron, calcium, potassium and titanium. By contrast, synthetic activated alumina consists essentially of alumina with virtually no significant impurities or at the most only a very small proportion of silica.

Researchers working on catalytic oxychlorination processes in the past have in some instances expressed a preference for the use of low-surface area alumina as catalyst supports, i.e., for supports having a surface area below 10 $m^2/g$, and especially between 2 and 5 $m^2/g$, as in U.S. Pat. No. 4,124,534. In other instances they have expressed a preference for high-surface area alumina as catalyst supports, i.e., for supports having a surface area of at least 100 $m^2/g$, as in U.S. Pat. No. 4,463,200. Low-surface area supports have been recommended mainly because they were thought to result in higher HCl conversions and lower carbon burning; see, for instance, U.S. Pat. No. 3,427,359 and French Patent No. 1,386,023. On the other hand, high-surface area supports have been recommended because they were through to contribute to an increased selectivity of the reaction toward the production of perchloroethylene as the desired product and a reduced formation of undesirable 1,1,2-trichloroethane and unsymmetrical tetrachloroethane, as indicated in U.S. Pat. No. 4,463,200.

Catalysts comprising a low-surface area support have been found to be relatively unstable in that such supports possess only a relatively small number of binding sites for retaining the active metal salts in the composition, and the resulting loss of the metal salts from such catalysts has been found to constitute a significant factor in causing corrosion of the metal reactors in which such oxychlorination reactions are generally carried out. In addition, especially when low-surface area supports such as diatomaceous earth or other silica-aluminas are used, high selectivities of perchlorethylene and trichloroethylene are only obtained at very high temperatures.

Catalysts based on high-surface area supports, which have been used successfully in producing ethylene dichloride at temperatures below 350° C., retain their catalytic salts well but have been found to cause substantial destruction of the feed material because of its oxidation to form carbon oxides. This becomes especially serious when unchlorinated ethane or ethylene or ethyl chloride is used as the feed to make more highly chlorinated hydrocarbons such as perchloroethylene and trichloroethylene, the production of which requires reaction temperatures near or above 400° C. in order to obtain good selectivity. Conversely, poor selectivity to the desired products has tended to occur when low-surface area aluminas were used as catalyst supports. Moreover, such prior catalyst compositions have been frequently found to have a relatively limited useful life because they have only moderate thermal stability and consequently tend to lose surface area and become sticky and corrosive to metal reactor walls as the oxychlorination process continues, especially at reaction temperatures above 350° C.

SUMMARY OF THE INVENTION

A primary object of the present invention is to provide an improved oxychlorination process for the production of perchloroethylene and trichloroethylene, which process avoids or substantially alleviates the disadvantages and problems of the prior art discussed above.

A more particular object is to provide an oxychlorination process for the production of perchloroethylene and trichloroethylene, wherein physical stability of the catalyst support is improved and corrosion of metal reactor surfaces is avoided or minimized.

Another object is to provide an improved, more stable catalyst for use in the production of perchloroethylene and trichloroethylene by oxychlorination, such that the disadvantages and problems encountered in the prior art may be avoided or substantially alleviated.

A corollary object is to provide an improved catalyst for the production of perchloroethylene and trichloroethylene by oxychlorination, which results in improved overall feed conversions and reduced reactor corrosion.

Another particular object is to provide an improved, microspheroidal alumina support for catalysts to be used in the production of perchloroethylene and trichloroethylene by catalytic oxychlorination, which alumina support possesses improved long-term surface area stability and consequently results in catalyst compositions which are operable over longer periods of time without becoming sticky and corrosive due to salt overload such as occurs when the surface area of the catalyst support becomes reduced in the process.

Another object is to provide an improvement in the production of perchloroethylene and trichloroethylene by oxychlorination of ethane, ethylene or partially chlorinated derivatives thereof, using a novel catalyst which gives improved performance in the form of reduced carbon burning and usually also increased conversion of hydrogen chloride or chlorine as well as higher total selectivity to the desired products.

In essence, the present invention provides an improved catalyst composition for the oxychlorination of $C_2$ hydrocarbons or partially chlorinated derivatives thereof at a temperature between about 250° and 470° C. This composition comprises as a support a rare-earth modified, substantially pure, high- to intermediate-surface area activated alumina, i.e., an activated-alumina containing only 0 to about 5 percent silica, most preferably not more than 0.5 percent silica, and from 0.2 to 10 percent of a certain class of rare earth, i.e., an oxide of a lanthanide other than cerium or an oxide of yttrium, that is, an element having an atomic number of 39, 57 or 59 through 71, preferably an oxide of neodymium or praseodymium, or most preferably an oxide of lanthanum. The use of the oxide of cerium (atomic no. 58) by itself is counterproductive but its admixture with one or more of the desirable Lanthanides is permissible in minor proportion, e.g., less than 50 percent, preferably less than 15 percent, based on the weight of the desirable Lanthanide Oxide or Oxides. Cerium oxide is at best a diluent. All these suitable lanthanide metals, including yttrium but excluding the ineffective cerium, are for convenience referred to in this specification and appended claims as "Lanthanides", and the corresponding oxides are referred to as "Lanthanide Oxides."

The present invention employing the incorporation of such Lanthanide Oxide as an integral part of the alumina support has been found to result in alumina supports possessing a remarkably improved thermal stability of their surface areas in oxychlorination reactions. No such stabilization of alumina supports is known to have been resorted to in the production of oxychlorination catalysts, as no logical reason for doing so was thought to exist since oxychlorination reactions are usually run at temperatures much below the normal 1200° C. transition temperature at which gamma-alumina changes to the low-surface-area alpha form. Thermal stabilization of alumina by incorporation of a Lanthanide Oxide such as lanthana is, however, not broadly new and has been employed in the manufacture of granula supports for platinum catalysts used in automotive exhaust canisters.

Another aspect of the present invention involves an improvement in the production of perchloroethylene and trichloroethylene by high-temperature oxychlorination of at least one $C_2$ hydrocarbon or a partially chlorinated derivative thereof, using as a catalyst a copper chloride-alkali metal chloride mixture deposited on a Lanthanide-modified alumina support and which catalyst support has its surface area closely controlled within a range that is in excess of 20 and less than 100 $m^2/g$. When such a catalyst composition is to be used in a fluidized-bed process, it is desirable that it be composed of microspheroidal particles having an average particle size of between about 30 and about 70 microns, as is otherwise well known. However, the present invention is also applicable to the coarser-size catalyst compositions customarily used in a fixed-bed oxychlorination process, e.g., particles having an average diameter in the range of from 1.0 to 10.0 mm.

Between about 10 and about 25 percent of the copper chloride-alkali metal chloride catalyst mixture (based on the weight of the total catalyst composition) is preferably loaded onto the novel support the catalyst salt mixture possessing a copper chloride/alkali metal chloride weight ratio of from 0.5:1 to 5.0:1, calculating the copper chloride as $CuCl_2$. Thus the use of the term "calculated as $CuCl_2$" signifies in this specification and claims that where cupric chloride ($CuCl_2$) is employed in the catalyst mixture, e.g., to obtain a copper chloride-/alkali metal chloride ratio of 1.2:1, 1.2 g cupric chloride is employed per gram of potassium chloride. If cuprous chloride (CuCl) is employed instead of $CuCl_2$ in making a catalyst mixture having the same copper chloride potassium chloride ratio of 1.2:1, just enough cuprous chloride (0.9 g CuCl) must be employed so that 1.2 grams of reacted cupric chloride will be present in the catalyst composition per gram of potassium chloride upon conversion of the cuprous chloride to cupric chloride in the oxychlorination reaction. Because modification of the alumina supports by an oxide of a Lanthanide in accordance with the present invention affords wide flexibility in the selectivity of the oxychlorination process in producing either more or less perchloroethylene relative to trichloroethylene, a significantly wider range of copper chloride/alkali metal chloride ratios is practical in the present invention than in the invention disclosed in the parent application Ser. No. 07/451,303, identified above.

A further improvement involves an oxychlorination catalyst which comprises a magnesium compound, such as magnesium chloride, magnesium nitrate or magnesium acetate as an additional component of the $CuCl_2$-KCl catalyst mixture that is loaded on an activated Lanthanide Oxide-modified alumina support. The desired weight ratio of potassium chloride to magnesium chloride is from 0.5:1 to 3.0:1 and is most preferably between about 0.5:1 and about 2.0:1, irrespective of the surface area of the support.

The desirable ratio of copper chloride to the sum of potassium chloride plus magnesium chloride in the catalytic salt mixture is within the range of 0.5:1 to 2.0:1, most preferably between 0.5:1 and 1.5:1, the specific, optimum ratio being dependent on whether trichloroethylene production is desired or is to be kept to a minimum. Increasing the ratio of copper chloride to the sum of potassium chloride plus magnesium chloride in the salt mixture to 1.5:1 or more favors lower trichloroethylene and higher perchloroethylene selectivity, whereas decreasing the ratio of copper chloride to the sum of potassium chloride plus magnesium chloride to 0.5:1 or less favors increased trichloroethylene and reduced perchloroethylene selectivity.

DESCRIPTION OF THE PREFERRED EMBODIMENTS

Perchloroethylene and trichloroethylene may be produced by catalytically oxychlorinating a $C_2$ hydrocarbon such as ethane, or ethylene, or an incompletely chlorinated derivative thereof such as ethyl chloride or ethylene dichloride (1,2-dichloroethane) or a mixture comprising two or more of these compounds. Ethane, ethylene and ethylene dichloride are particularly preferred feedstocks. As used in this specification and in the appended claims, the term "C₂ Hydrocarbon" means and includes ethane, ethylene, and any partially chlorinated derivative thereof. Of course, recycle chlorocarbon streams from the process can be used as feed sources. Because the production of perchloroethylene and trichloroethylene by oxychlorination is a highly exothermic process, it is best carried out using a solid catalyst in a fluidized bed which, unlike a fixed bed, minimizes the formation of undesirable hot spots and facilitates the removal of the heat of reaction by means of heat exchangers, as is otherwise well known in the art. See for example, M. Leva, "Fluidization", McGraw-Hill 1959, pp. 6, 208-209.

Such oxychlorination is desirably carried out at temperatures of between about 250° and about 470° C., preferably between 370° and 450° C., and most preferably between about 400° and 430° C. Reaction pressure may be atmospheric, subatmospheric or superatmospheric, but preferably is maintained between about 1 and 20 atmospheres (absolute), more preferably between about 1 and 6 atmospheres.

The oxychlorination reaction is generally conducted for a time sufficient to maximize the production of perchloroethylene and trichloroethylene based on carbon utilization, and preferably such that a mole ratio of perchloroethylene to trichloroethylene in the product is kept above about 5:1 when wishing mainly to produce perchloroethylene, and is kept at about 1:1 when wishing to produce trichloroethylene as a co-product. For example, the superficial reaction zone residence time may be from several seconds to several minutes, e.g., from about 2 to 60 seconds, preferably from about 10 seconds up to about 30 seconds.

Oxygen may be supplied for the reaction as pure oxygen gas or more commonly as an oxygen-containing gas, e.g., air or oxygen-enriched air. As is otherwise well known in the art, the ratio of total feed of oxygen to total feed of C₂ Hydrocarbon is a variable number which depends upon the specific composition of the feed and other process design factors. The oxychlorination reaction may be conducted with an amount of oxygen that is at least equal to the stoichiometric amount required to completely oxychlorinate the organic feed to the ratio of trichloroethylene and perchloroethylene desired while at the same time converting all displaced hydrogen to water.

Typically the amount of oxygen supplied ranges between this stoichiometric amount and up to about 200% in excess of this amount, preferably from about 10 to about 50% in excess of stoichiometric. For instance, when making perchloroethylene by oxychlorinating ethylene, the reaction may be represented by the equation

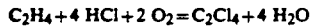

$$C_2H_4 + 4\ HCl + 2\ O_2 = C_2Cl_4 + 4\ H_2O$$

In such a case it is preferred to use from 2.2 to 3 moles of oxygen per mole of ethylene feed.

Hydrogen chloride o chlorine or both are also supplied to the reaction mixture in addition to the organic feed material and oxygen. The ratio of total feed of chlorine and/or hydrogen chloride to total feed of organic feedstock again is a variable number which depends upon the specific composition of the feed and other process design factors, as is well known in the art. The oxychlorination reaction is typically conducted with an amount of chlorine and/or hydrogen chloride adjusted to reflect the ratio of trichloroethylene and perchloroethylene desired, that is, at least equal to about 50% of the stoichiometric required to oxychlorinate the organic starting material completely to perchloroethylene.

For example, when ethylene dichloride is being catalytically oxychlorinated to perchloroethylene, it is preferred to conduct the reaction at a temperature between about 400° and 430° C. and maintain the mole ratio of hydrogen chloride to ethylene dichloride above about 1.6, preferably from between about 1.6 to about 1.9, while maintaining the molar ratio of oxygen to ethylene dichloride between about 1.5 and 2.2.

Perchloroethylene and trichloroethylene may be recovered from the reaction product stream by any suitable technique known in the art. Thus, the effluent from the reactor may be passed through a cooler and a condenser to a phase separator which collects the condensed chlorohydrocarbons and hydrochloric acid. The chlorohydrocarbon stream from the phase separator may then be neutralized, dried, and sent to a fractional distillation system for purification and recovery of perchloroethylene and trichloroethylene.

When producing ethylene dichloride from ethylene by oxychlorination, commercial processes have commonly been conducted at temperatures below 300° C., i.e., at relatively low temperatures, and have in the past employed copper chloride-containing catalysts based on high-surface-area alumina. Other such processes have used naturally occurring minerals for catalyst supports. In any case, to be commercially useful, catalysts used in oxychlorination processes must have long-term surface area stability. Otherwise they become inoperable because of stickiness from salt overload when the surface are of the support shrinks excessively. Loss of surface area in alumina catalyst supports usually occurs because of a phase change from the gamma phase to the more dense alpha-alumina phase which has a very low-surface area range.

In the more recent adaptation of the oxychlorination reaction to the production of perchloroethylene and trichloroethylene, temperatures of around 420° C. have been favored, i.e., temperatures which are significantly higher than when making ethylene dichloride but still well below 1200° C., i.e. well below temperatures that are generally considered necessary to produce alpha-alumina from the gamma phase by heat alone.[1] The transition of gamma to alpha-alumina has also been reportedly achieved in the 375° to 425° C. range by hydrothermal treatment, but only under high pressures of at least 10 atmospheres.[2] HCl has also been reported to cause the transition from gamma to alpha-alumina at well below 1200° C., e.g., at 850° C.[3] Based on such data, the logical expectation has been that the stability of an alumina-based catalyst at low pressures, e.g., less than seven atmospheres, would be substantially as good in an oxychlorination process conducted at between about 370° and 470° C. as it has been known to be in oxychlorination processes conducted at or below 300° C. However, this expectation has been found to be misplaced.

[1] Karl Wefers et al, "Oxides and Hydroxides of Alumina," Tech. Paper No. 19, Alcoa Research Laboratories, 1972, Table 14, page 43.
[2] Allen S. Russell. "Alumina Properties," Tech, Paper No. 10, Alcoa Research Laboratories, 1953, page 6.
[3] Gitzen, "Alumina as a Ceramic Material," Ceramic Society, Golumbus, Ohio, Page 24.

The simultaneous presence of steam and HCl in an oxychlorination process apparently can effect the transition from gamma to alpha-alumina at even lower temperatures, since a large decrease in surface area, from 73 m$^2$/g to a mere 9 m$^2$/g, has been observed in a copper chloride-potassium chloride catalyst based on a gamma-alumina support in only 288 hours under oxychlorination conditions of 418° C. and about 4 atmospheres pressure. Such a thermochemical degradation of conventional oxychlorination catalyst compositions at temperatures near or above 400° C. has therefore been thought to make the production of perchloroethylene or triohloroethylene by oxychlorination uneconomical with this type of catalyst.

As indicated earlier herein, the essence of the present invention lies in providing a special, improved catalyst composition for such high-temperature oxychlorination of C$_2$ Hydrocarbons. This composition comprises a copper chloride-alkali metal chloride catalyst mixture deposited on a carrier or support which is characterized by being composed essentially of Lanthanide Oxide-modified alumina having a properly selected surface area. In particularly preferred catalyst compositions the catalyst mixture comprises not only copper chloride and potassium chloride, but also a certain proportion of magnesium chloride.

In U.S. Pat. No. 4,463,200 it has been disclosed that in the manufacture of perchloroethylene by oxychlorination the use of a copper chloride-potassium chloride catalyst supported on an activated alumina support having a surface area of at least 100 m$^2$/g and preferably between 150 and 250 m$^2$/g results in a significant reduction in the formation of undesirable by-products such as 1,1,2-trichloroethane or 1,1,1,2-tetrachloroethane and that this kind of high-surface-area support simultaneously favors a high molar ratio of perchloroethylene to trichloroethylene in the product. However, while such catalyst compositions using a high-surface-area support result in excellent chlorine utilization, we have found them to promote excessive destruction of the organic feed material by converting it to oxides of carbon especially so when operating at conditions selected to produce a high carbon selectivity to trichloroethylene. Because of this, we have found supports advantageous not only in the practice of the invention described and claimed in our parent application, Ser. No. 07/451,303, but also in the invention described in the instant application.

More particularly, as already indicated in the Summary Section of this specification, it has now been discovered that an improved catalyst for the manufacture of trichloroethylene and perchloroethylene by oxychlorination in a fluidized bed can be obtained by using as the catalyst support an activated, Lanthanide Oxide-modified alumina possessing a surface area that is in excess of 20 m$^2$/g and less than 100 m$^2$/g, preferably between about 20 m$^2$/g and about 80 m$^2$/g, and most preferably between about 25 and 60 m$^2$/g.

Still more specifically, it has now been found that catalysts based on alumina supports can be significantly improved in terms of their mechanical attrition resistance as well a their resistance to thermochemical degradation in an oxychlorination process when a minor proportion, ranging from 0.2 to 10%, and preferably 0.5 to 5.0% (calculated as oxide), of a salt o oxide of the group of "Lanthanides" defined in the summary portion of this specification is integrally or intrinsically incorporated in the alumina. This can be accomplished, for example, by impregnation of the alumina with a solution of the Lanthanide salt and by subsequent calcination, or by co-precipitation of the alumina and the Lanthanide Oxide from solution and subsequent calcination at a temperature of at least 800° C., preferably between 1000° and 1500° C., most preferably at about 1200° C. When the Lanthanide Oxide is intrinsically incorporated and distributed in the alumina the Lanthanide is substantially insoluble and cannot be selectively removed by extraction with water or by superficial abrasion of the catalyst particles.

This kind of Lanthanide Oxide addition to the alumina at these concentrations has been found to produce a most beneficial improvement in the properties of the support without any adverse side effect on the desired functioning of the oxychlorination process. This has been found true not only under moderate temperature conditions but also under high temperature conditions such as those normally used in the production of perchloroethylene and trichloroethylene by oxychlorination of C$_2$ Hydrocarbons. Catalyst compositions based on these particular Lanthanide-modified alumina supports showed no noticeable loss of surface area in oxychlorination runs as long as about 1000 hours, and exhibited excellent resistance to attrition. By contrast, mere impregnation of a Lanthanide salt on an alumina support will leave the Lanthanide in a form that is susceptible to removal from the alumina support or the final catalyst composition by superficial attrition or by dissolution in water or other solvent and will not result in a comparable improvement.

The aluminas used in preparing such catalyst supports are preferably first activated by heating at a suitable elevated temperature at which the alumina is dehydrated, as is otherwise known in the art. For instance, such activation can be conducted at about 400° or higher, e.g., at 500° or 600° C. However, unactivated aluminas can also be used.

Preparation of alumina-based catalyst supports is of course known in the prior art. Suitable processes commonly used for the preparation of alumina supports are described, for instance, in Applied Industrial Catalysis, Volume 3: "Alumina for Catalysts-Their Preparation and Properties" pp. 63-111. In practicing the present invention, stable catalysts can be obtained when a Lanthanide salt is integrally incorporated into the alumina before spray-drying of the aqueous alumina gel or other forming operation for the support, followed by calcination of the resulting microspheres to the desired surface area. Acceptable results can also be obtained by catalyst compositions prepared with alumina supports in which the Lanthanide Oxide is integrally incorporated by: (a) adding through aqueous or solvent impregnation of a Lanthanide salt to the formed support before activation and then calcining to the desired surface area, or (b) adding a Lanthanide salt to the activated support and recalcining at a temperature above 800°, e.g., in a range between about 1000° and 1500° C. In imparting stability to the alumina, these methods of modified alumina preparation produce results that are distinctly different from, and otherwise better than, merely loading a Lanthanide salt on the finished support as part of the catalyst formulation such as has heretofore been proposed in U.S. Pat. No. 3,210,431.

Increased amounts of a suitable Lanthanide Oxide have been found to lessen the rate of surface area shrinkage with respect to time. Increased stability can thus be imparted by the inclusion of a larger concentration of a suitable Lanthanide Oxide in the catalyst support.

When a Lanthanide Oxide-modified alumina support having a surface area in the range of from more than 20 to less than 100 m²/g, and most preferably between 25 and 60 m²/g, is loaded with a proper amount of a catalytic mixture of copper chloride and potassium chloride and used as a catalyst in a fluidized state in the manufacture of trichloroethylene and perchloroethylene by oxychlorination, overall feed conversions are maintained at high levels over extended run times along with a substantial and unexpected reduction in metal corrosion rates. Good thermal stability of the catalyst and the concomitant low corrosion rate are of course greatly desired in large-scale industrial oxychlorination reactors but have been difficult to achieve.

As already stated in the summary section of this specification, the catalytic metal salts are loaded onto the supports possessing the selected surface area at a concentration of 10 to 25 percent, with the weight ratio of copper(II) chloride to potassium chloride in the catalytic salt mixture being from 0.5:1 to 5.0:1.0.

The most suitable amount of the catalytic salts used for any particular catalyst composition is dependent on the surface area of the support. Supports having a surface area greater than 100 m²/g can support up to 30 or 35 percent of the copper chloride and potassium chloride salts without experiencing fluidization problems. However, such relatively high catalyst loadings have been found to cause the microspheroidal catalyst particles to become sticky and difficult to maintain in the fluidized condition if loaded onto a support having a surface area of less than 100 m²/g. Accordingly, for a catalyst support having a surface area in the range preferred in the present invention, i.e., in excess of about 20 but less than about 100 m²/g, a total salt loading of between 10 and 25 percent based on the weight of the finished catalyst composition is preferred. In the most preferable range, i.e., with surface areas between about 25 and 60 m²/g, a total salt loading of between 15 and less than about 20 percent based on the weight of the finished catalyst is best used. Of course, it is important in such a case for the surface area of the catalyst support to remain relatively stable, as the present invention makes possible.

When the oxychlorination reaction is carried out in a fluidized bed of microspheroidal catalyst, the $C_2$ Hydrocarbon as defined above, chlorine and/or a chlorine-containing feed gas, and air or oxygen, all enter a lower portion of the reaction zone at a combined velocity above the minimum fluidization velocity of the catalyst. Depending on which particular chlorocarbon is desired as the principal product, the ratio of $C_2$ Hydrocarbon feed and chlorine-containing feed can be varied to control the degree of chlorination, i.e., to achieve the desired trichloroethylene/perchloroethylene split.

The invention will next be illustrated by several working examples.

CATALYST AND LIFE TESTS

EXAMPLE 1

Preparation of Catalyst For Use In 15.2-cm Diameter Reactor

In preparing catalyst compositions representative of the prior art for use in Runs I-1 and I-2 (TABLE I), a 42-kg quantity of a commercial microspheroidal alumina support, designated as Harshaw Al-1401-P and composed essentially of high-purity alumina without any Lanthanide Oxide or salt, was placed, either as such or after calcination to obtain a certain reduced surface area, in an epoxy-coated steel tray capable of being heated with steam pipes fastened beneath it. For use in Run I-3, 4.9 weight percent Lanthanide Oxide was additionally integrally incorporated in the alumina support by impregnation with a Lanthanide salt solution and subsequent calcination. An aqueous solution of 10.7 kg of copper(II) chloride dihydrate, 5.6 kg of potassium chloride and 20.1 kg of water was poured over the support and mixed in thoroughly with a small rake. The catalyst composition was dried to a uniform brown color with 8-atmosphere steam in the heating pipes under the pan. Target loading for this catalyst was 15.0 and 10.0 weight percent copper and potassium chloride respectively as calculated by the total weight of the anhydrous metal chlorides and the alumina or modified-alumina support.

The actual catalyst compositions produced, the conditions used in the runs in which they were tested as well as the results obtained in these tests are shown in Table I, Runs I-1, I-2, I-3. A description of the reactor and test conditions used in these tests is given in Example 3 below.

As the results show, catalyst compositions used in Runs I-1 and I-2 which were prepared from high purity alumina, suffered major reductions in surface area, i.e., they showed themselves to be thermally quite unstable under the conditions of these tests. This is in sharp contrast to the novel catalyst composition using the Lanthanide Oxide-modified catalyst support described in Example and tested in Run I-3. The stability of Lanthanide Oxide-modified catalysts supports is further demonstrated in later examples.

EXAMPLE 2

Preparation of Catalyst For Use In 5.1-cm Diameter Reactor 3,050-g samples of various microspheroidal alumina supports modified by incorporating therein various amounts of Lanthanide Oxide prior to calcination were placed in heavy-gauge plastic bags. An aqueous solution of 773 g copper(II) chloride dihydrate, 407 g potassium chloride and 1455 g water was then added to each of the alumina samples in the plastic bag. Sufficient solution was present to moisten all of the alumina. Each preparation was thoroughly mixed by hand kneading, placed in a glass dish and dried overnight at 150° C. When the alumina support had a surface area in the range from about 150 to 200 m²/g, target loadings of catalysts prepared therewith were 15.0 and 10.0 percent copper chloride and potassium chloride, respectively, calculated as the weights of the anhydrous metal chlorides based on the weight of the finished catalyst. Salt loadings were adjusted dependent on the surface area of the support. Thus, for instance, with alumina supports having surface areas in the range from about 20 to about 100 m²/g, significantly lower loadings, e.g., about 9 percent $CuCl_2$, 3.7 to 6.5 percent KCl, and, optionally, 4.1 to 6.5 percent $MgCl_2$, were successfully used.

The actual catalyst compositions produced, the conditions used in the runs in which they were tested as well as the results obtained in these tests are shown in Table I, Runs I-4, I-5 and I-6. A description of the test reactor is given in Example 4 below.

EXAMPLE 3

Catalyst Life Test In 15.2-cm Fluidized Bed Oxychlorination Reactor

The selected catalyst charge is listed in Table I, I-1, I-2 or I-3 and described in Example I was used in the quantity described in Table II and tested in the reactor identified in Table II.

The selected charge was loaded into a pressurizable reactor fabricated from 15.2-cm diameter Inconel 600 nickel alloy pipe 396 cm in length. Welded into the top and bottom of this reactor section were four 1.9-cm diameter tubes running the length of the section and standing out 2.5 cm from the wall. "Dowtherm A" heat transfer medium was circulated through these tubes for cooling. A distributor was flanged to the bottom of the reactor section and an enlargement section to the top. The enlargement tapered from the 15.2-cm pipe section through a 60-degree cone into a cylinder 40.6 cm in diameter and 61.0 cm high. The effluent line of this reactor was equipped with a cyclone with a catalyst return leg, a fines filter and a pressure control valve. Thermowells were welded into the side of the reactor tube at various levels. The reactor and accessory equipment were electrically heated and insulated.

The quantities and rates of catalyst charged and feeds introduced into the 15.2 cm diameter reactor, as well as the average operating conditions, are shown under Run No. II-3 in Table II below. Catalyst samples were removed periodically through a valve without shutdown.

EXAMPLE 4

Catalyst Life Test in 5.1-cm Fluidized-Bed Oxychlorination Reactor

A pressurizable oxychlorination reactor fabricated from 5.1-cm diameter Inconel 600 nickel alloy pipe 396 cm in length was used in measuring the life of various other catalysts in this example. Welded around the reactor tube was a pressurized 10.2-cm pipe jacket connected into a thermosyphon filled with "Dowtherm A" heat transfer medium for cooling. The reactor was equipped with a distributor at the bottom and an enlargement at the top. The enlargement was 15.2 cm in diameter and 122 cm long, tapering downward to its flange connection with the 5.1-cm reactor tube. The effluent line was equipped with a cyclone, fines pot, fines filter and pressure control valve. A 0.6-cm Inconel tube, extending the length of the reactor tube, contained a sliding thermocouple. The reactor, effluent line and accessory equipment were electrically heated and insulated.

Various microspheroidal catalysts (see Table I, Runs I-4, I-5, I-6) in the quantity prepared in Example 2 were loaded into the reactor. The reactor was periodically shut down and depressurized for removal of catalyst samples for surface area analysis. The quantities of catalyst charged, rates of feed introduced into the 5.1 cm reactor, as well as the operating conditions are shown under Run No. II-2 in Table II below.

As the reaction aging data in Table I show, the catalyst composition tested in Run I-4, prepared from unmodified high purity alumina, suffered very major reductions in surface area, i.e., this catalyst showed itself to be thermally quite unstable under the conditions of these tests. This is in sharp contrast to the novel catalyst compositions using Lanthanide Oxide-modified catalyst supports described in Example 2 and tested in Run I-5 and I-6.

A Lanthanide Oxide-stabilized catalyst life test was also completed using a 3.8-cm diameter reactor, Run No. I-7, Table I. The reactor is fully described in Example 8 with run conditions described in Table II, run No. II-3. Comparative tests have shown that similar performance is obtained with the 3.8-cm, 5.1-cm and 15.2-cm diameter reactors. Results obtained in Run I-7 again confirm the stability of Lanthanide Oxide-stabilized catalysts. One should note that the tests were conducted in all three reactors under reaction conditions that were identical or very similar, except that in the runs conducted in the 3.8 cm reactor (Table II, Run No. II-1) the catalyst charge was much less and the superficial linear velocity was only about half that used in the tests conducted in the 5.1 cm and the 15.2 cm reactors (Table II Runs No. II-2 and II-3).

TABLE I

Properties of Supports and Catalysts Before and After Reaction Aging

| Run Area No. | Support | Lanthanide Oxide, Weight Percent | Initial Surface Area, $m^2/g$ Support | Initial Surface Area, $m^2/g$ Catalyst | Catalyst Salt Loading $CuCl_2$ Weight Percent | Catalyst Salt Loading KCl Weight Percent | Catalyst Salt Loading $MgCl_2$ Weight Percent | Run Time, Hours | Run Temp., °C. | Final Surface of Catalyst, $m^2/g$ |
|---|---|---|---|---|---|---|---|---|---|---|
| | | | Tested in the 15.2-cm diameter reactor | | | | | | | |
| I-1 | Alumina A | 0.0 | 190 | 73 | 15.0 | 10.0 | — | 288 | 418 | 9 |
| I-2 | Alumina B | 0.0 | 166 | 72 | 15.0 | 10.0 | — | 540 | 418 | 16 |
| I-3 | Alumina E | 4.9 (1) | 47 | 27 | 9.1 | 4.1 | 4.1 | 950 | 418 | 26 |
| | | | Tested in the 5.1-cm diameter reactor | | | | | | | |
| I-4 | Alumina C | 0.0 | 35 | 21 | 8.8 | 3.7 | — | 873 | 410 | 14 |
| I-5 | Alumina D | 4.6 (2) | 55 | 36 | 9.4 | 4.4 | 4.4 | 394 | 410 | 39[a] |
| I-6 | Alumina E | 4.9 (1) | 47 | 28 | 9.1 | 4.1 | 4.1 | 970 | 410 | 31[a] |
| | | | Tested in the 3.8-cm diameter reactor | | | | | | | |
| I-7 | Alumina F | 2.5 (3) | 92 | 33 | 9.0 | 6.5 | 6.5 | 223 | 411 | 43[a] |

[a]The higher catalyst surface at the end of the runs than initially is thought to be due to pore opening caused by dehydration and redistribution of the catalyst salts; some variability may also be due to non-uniform sampling.
(1) Approximately 58.37% lanthanum oxide, 19.59% neodymium oxide, 14.08% cerium oxide and 7.96% praseodymium oxide (by x-ray emission analysis)
(2) Essentially pure lanthanum oxide
(3) 49.6% lanthanum oxide, 50.0% cerium oxide and 0.4% neodymium oxide (by x-ray emission analysis)

TABLE II

Run Conditions for Oxychlorination Catalyst Life Studies

| Run No. | II-1 | II-2 | II-3 |
|---|---|---|---|
| | Reactor Diameter | | |
| | 3.8-cm | 5.1-cm | 15.2-cm |
| Reaction Parameters | | | |
| Ethylene Dichloride Feed | | | |
| Catalyst Charge, kg | 1.1 | 4.1 | 38.6–61.3 |
| Temperature, °C. | 411 | 410 | 418 |

TABLE II-continued

| | II-1 | II-2 | II-3 |
|---|---|---|---|
| | \multicolumn{3}{c}{Reactor Diameter} | | |
| Run No. | 3.8-cm | 5.1-cm | 15.2-cm |
| Pressure, atm. | 60 | 60 | 60 |
| Catalyst Bed Height, cm | 122 | 259 | 274–396 |
| Superficial Linear Velocity, cm/sec | 8.5 | 18.3 | 18.3 |
| Residence Time, seconds | 14 | 14 | 14–22 |
| HCl/Ethylene Dichloride Molar Ratio | 1.2–1.68 | 1.2–1.68 | 1.35 |
| HCl/Oxygen Molar Ratio | 0.84–0.95 | 0.96 | 0.95 |
| When Ethylene Dichloride Feed Was Replaced by Ethylene: | | | |
| HCl/Ethylene Molar Ratio | — | — | 2.85 |
| HCl/Oxygen Molar Ratio | — | — | 1.60 |

Referring to Table I, Aluminas A, B and C are controls, showing the losses of surface area obtained when high- and intermediate-surface area aluminas containing no Lanthanide as a stabilizer were used as catalyst supports under substantially identical conditions in the high temperature oxychlorination reaction to make perchloroethylene and trichloroethylene. Aluminas D and E were experimental stabilized alumina supports containing 4.6 and 4.9 percent respectively, of Lanthanide Oxide, and Alumina F was a Lanthanide Oxide-stabilized support prepared to applicants' order by Akzo Chemie in the Netherlands, containing 2.5 percent Lanthanide Oxide. For comparison, the initial surface areas of the catalyst compositions based on Aluminas D, E and F were of approximately the same magnitude as that of the catalyst composition based on Alumina C (control). The results in Table I show a very large degree of surface area shrinkage in the case of catalysts made with Aluminas A, B and C (Runs I-1, I-2, and I-4), as opposed to virtually no significant shrinkage in the case of catalysts made with the Lanthanide Oxide-stabilized Aluminas D, E and F (Runs I-3, I-5, I-6 and I-7) when used in oxychlorination runs from about 400 to 1000 hours in duration under similar conditions.

The amount of Lanthanide Oxide, if any, incorporated in each alumina support tested is shown in Table I. The Lanthanide Oxide employed in the preparation of Alumina D consisted essentially of pure lanthanum oxide. As determined by x-ray emission analysis, the Lanthanide Oxide employed in the preparation of Alumina F consisted of 49.6 weight percent lanthanum oxide, 50.0 percent cerium oxide and 0.4 percent neodymium oxide.

The Lanthanide oxide employed in the preparation of Alumina E contained a major proportion of lanthanum oxide and minor proportions of oxides of praseodymium, neodymium as well as cerium. More specifically, its use resulted in a modified alumina support in which the 4.9 weight percent Lanthanide Oxides ($Re_2O_3$) were distributed as follows as determined by X-ray emission analysis:

| Lanthanide Oxide In Alumina Support | Weight Percent |
|---|---|
| $La_2O_3$ | 2.86 |
| $CeO_2$ | 0.69 |
| $Pr_6O_{11}$ | 0.39 |
| $Nd_2O_3$ | 0.96 |
| Total | 4.90 |

As can be seen from Table I, the catalyst compositions based on the novel Lanthanide Oxide-modified aluminas (Runs I-3, I-5, I-6 and I-7) exhibited excellent stability of surface area.

STABILITY AND ATTRITION TESTS

EXAMPLE 5

Thermal Stability Tests For Catalyst Support

A 20.0-g sample of commercial "Catapal SB", an unactivated microspheroidal, high-purity, Boehmite alumina support manufactured by Continental Oil Company, was weighed into a 100-ml Coors AD-998 alumina crucible. In a 50-ml beaker 1.78 g $NdCl_3.6H_2O$ and 11 ml water were mixed to form a solution. The solution was poured into the crucible with the alumina and mixed thoroughly. The water adsorption capability of the alumina was 0.59 ml of water per gram. The above solution was just enough to bring the mixture to the point of incipient wetness. The resulting dough-like mixture was dried for two hours at 125° C. The amount of Lanthanide compound was calculated to produce the desired percentage of Lanthanide Oxide based on the ignited anhydrous weight of the "Catapal" support. By preliminary test it was determined that the "Catapal" alumina support as received lost 30 percent of its weight on calcination at 1200° C.

The same "Catapal SB" alumina support was similarly treated with various concentrations of other Lanthanide metal salts, namely, yttrium, lanthanum, cerium, praseodymium and with a commercial mixture comprising principally lanthanum accompanied by smaller amounts of neodymium, praseodymium, and cerium. To screen stabilization effects more efficiently over a short period of time, dried samples of the Lanthanide-treated alumina were heated in a Lindbergh high-temperature oven for three hours at 1200° C., converting all Lanthanide compounds to the oxides and integrally incorporating them in the alumina support. Single-point B.E.T. (Brunauer, Emmett and Teller) Theory surface areas of the various resulting Lanthanide Oxide-containing supports were measured. The results of these thermal tests are shown in Table III.

Table III shows that measurable stabilization began with only 0.25 percent $La_2O_3$ (Sample 10) in the catalyst support and, as compared with the control, began to assume major and increasing importance when present in the 0.5 to 6 percent range. Concentrations between about 0.5 and about 3 percent of Lanthanide Oxide are preferred, as the incremental benefit obtained at higher concentrations is usually small. Results in Table III further show that $Y_2O_3$ also stabilized the support but not as well as the other Lanthanides used, namely, lanthanum, neodymium, praseodymium, and a commercial mixture comprising all three.

However, contrary to the action of all the other Lanthanide oxides tested, cerium surprisingly showed itself to be detrimental in that it actually increased the loss of surface area as compared with the control, rather than decreasing it. Lanthanum, praseodymium and neodymium oxides, mixed Lanthanide Oxides containing two or more of these three Lanthanides, as well as a mixed Lanthanide Oxides containing a moderate to low amount of cerium oxide all were very effective in stabilizing the support, but the use of lanthanum oxide is preferred.

TABLE III

Thermal Stabilization of an Alumina Support by Various "Lanthanide Oxides" Heated at 1200° C. for Three Hours

| Sample No. | "Lanthanide" Salt Used As Modifier | "Lanthanide Oxide" (as sesquioxide except as noted) Wt %[a] | Surface Area m²/g |
|---|---|---|---|
| 1 (Control) | None | 0 | 6.0 |
| 2 | NdCl₃ | 5.6 | 38.7 |
| 3 | NdCl₃ | 2.9 | 35.0 |
| 4 | YCl₃ | 5.6 | 19.2 |
| 5 | LaCl₃ | 5.6 | 42.0 |
| 6 | Ce(NO₃)₃ | 5.6[b] | 4.4 |
| 7 | PrCl₃ | 5.6[c] | 35.4 |
| 8 | "MolyCorp 5240"[d] | 5.6 | 41.0 |
| 9 | "MolyCorp 5240"[d] | 2.7 | 45.0 |
| 10 | La(NO₃)₃ | 0.25 | 9.5 |
| 11 | La(NO₃)₃ | 0.5 | 13.3 |
| 12 | La(NO₃)₃ | 1.00 | 25.9 |
| 13 | La(NO₃)₃ | 2.50 | 39. |
| 14 | La(NO₃)₃ | 4.3 | 39.0 |

[a]Calculated assuming a 30 weight percent loss on ignition, the amount experimentally determined for the support at 1200° C.
[b]Calculated as cerium oxide, CeO₂; not as sesquioxide
[c]Calculated as praseodymium oxide, Pr₆O₁₁; not as sesquioxide
[d]Mixture of Lanthanide chlorides; (46% Lanthanide Oxide equivalent) described as follows:
La₂O₃   28.0%
CeO₂    4.5%
Pr₆O₁₁  3.5%
Nd₂O₃   10.0%

EXAMPLE 6

Comparative Attrition Test

Pure spray-dried alumina, silica-stabilized alumina and Lanthanide Oxide-stabilized alumina supports were compared in terms of their respective attrition resistances, the results being shown in Table IV below. The stabilized supports were prepared using spray-dried alumina-base materials and alumina-base materials that were intrinsically modified with either silica or a Lanthanide Oxide by impregnation and calcining. The method of preparing such silica-modified alumina materials is described in copending application Ser. No. 07/451,303 filed Dec. 15, 1989 while preparation of Lanthanide Oxide-modified aluminas is described in the present specification, notably in Example 5 hereinabove. As an example, the Lanthanide Oxide used in making stabilized alumina supports, IV-13, IV-14, IV-17 and IV-18, Table IV, was a mixture having the following composition: La₂O₃, 60%; CeO₂, 10%; Pr₆O₁₁, 7.5%; and Nd₂O₃, 22.5%. It was included in the alumina in a concentration of 4% based on the total weight of the support, the other 96% being essentially pure alumina. The other Lanthanide-stabilized supports, IV-9, IV-10, IV-11, IV-15 and IV-16 were prepared using a similar Lanthanide Oxide mixture or one higher in lanthanum oxide.

The attrition test procedure used was based on the procedure described in the article by W. L. Forsythe, Jr. and W. F. Hertwig "Attrition Characteristics of Fluid Cracking Catalysts. Laboratory Studies," *Industrial and Engineering Chemistry*, 1200–6, June 1949.

The Lanthanide Oxide-stabilized intermediate-surface area aluminas No. IV-9 through IV-18 have been found to exhibit very low attrition in these attrition tests. This contrasts with the very high degree of attrition obtained with the support used in the best silica-stabilized aluminas IV-6, IV-7 and IV-8. While the unmodified aluminas show somewhat better attrition resistance than the silica-modified aluminas, the latter do have the advantage of being substantially more thermally stable in the oxychlorination reactor than the unmodified aluminas. But the Lanthanide-modified aluminas are, with the exception of IV-9, surprisingly superior to all the other compositions of both of the other types not only in terms of thermal stability but also in terms of attrition resistance. As regards support IV-9, it may be said that this was obtained in the first experimental preparation of this material and is not believed to be properly representative. All subsequent preparations of this material have consistently produced supports with much lower attrition indices, i.e., much higher attrition resistance, as shown by supports IV-10 through IV-18.

TABLE IV

ATTRITION TESTS

| Sample No. | Surface Area | Kind of Stabilizer | Stabilizer % | Attr. Index[a] |
|---|---|---|---|---|
| Alumina supports | | | | |
| IV-1 | 190 | none | — | 26.3 |
| IV-2 | 196 | none | — | 35.5 |
| IV-3 | 34.4 | none | — | 29.4 |
| IV-4 | 34.5 | none | — | 25.4 |
| IV-5 | 36.2 | none | — | 15.7 |
| IV-6 | 34.7 | SiO2 | 1.5 | 31.7 |
| IV-7 | 54 | SiO2 | 1.6 | 32.5 |
| IV-8 | 55 | SiO2 | 1.5 | 34.5 |
| IV-9 | 55 | Lanthanide Oxide | 4.6 | 17.1 |
| IV-10 | 47 | Lanthanide Oxide | 4.9 | 3.8 |
| IV-11 | 52 | Lanthanide Oxide | 4.6 | 4.6 |
| IV-12 | 78 | Lanthanide Oxide | 4.6 | 7.2 |
| IV-13 | 69 | Lanthanide Oxide | 4.0 | 7.2 |
| IV-14 | 58 | Lanthanide Oxide | 4.0 | 3.1 |
| IV-15 | 60 | Lanthanide Oxide | 4.6 | 0.9 |
| IV-16 | 47.8 | Lanthanide Oxide | 4.6 | 7.0 |
| IV-17 | 43.9 | Lanthanide Oxide | 4.0 | 1.5 |
| IV-18 | 44.9 | Lanthanide Oxide | 4.0 | 0.3 |

[a]Standard Oil of Indiana Procedure (Forsythe and Hertwig)

EFFECT OF SURFACE AREA ON CATALYST PERFORMANCE

EXAMPLE 7

Preparation of Catalyst For Use In 3.8-cm Diameter Reactor

An aqueous solution of 129 g of cupric chloride dihydrate, 156 g of magnesium chloride hexahydrate and 73.1 g of potassium chloride in 238 g of water was prepared and added to Alumina F described in Table I above, a heavy plastic bag containing 877 g of Alumina F described in Table I above, a Lanthanide oxide-stabilized alumina support composed of 2.5 percent Lanthanide Oxide and about 97.5 percent alumina, and having a surface area of 92 m²/g.

The constituents were kneaded to a uniform color and consistency in the closed bag. Sufficient solution was present to create the consistency of dough. The uniform mixture was placed in a glass dish in an oven at 150° C. and dried overnight. The target composition for this catalyst, designated catalyst "I-7" in Table I, was copper(II) chloride, 9.0%; potassium chloride, 6.5%; and magnesium chloride, 6.5%; all calculated on the basis of the weights of anhydrous metal chloride and the alumina support.

EXAMPLE 8

Catalyst Performance Test in the 3.8-cm Diameter Fluidized-Bed Oxychlorination Reactor The selected microspheroidal catalyst charge (catalyst I-7, Table I), was loaded into a pressurizable reactor constructed from 3.8-cm diameter Inconel 600 nickel alloy pipe 122 cm in length. An enlargement 15.2 cm in diameter and 25.4 cm in length was welded to the top of the 122-cm reaction tube. Cooling for removal of heat of reaction was provided by a 0.6-cm diameter tube passing through the head of the reactor and extending to within 2.5 cm of the bottom feed distributor. Inside the 0.6-cm diameter tube was placed a 0.3-cm diameter tube through which cooling air was passed and allowed to escape through the annulus between the outer and inner tubes. To the head of the reactor was attached a cyclone, fines filter and pressure control valve. A 0.6-cm diameter Inconel tube extending the length of the enlargement and reaction tube contained a sliding thermocouple. The reactor, enlargement, cyclone, fines filter and pressure control valve were electrically heated and insulated. The reactor was shut down and depressurized for adding or removing catalyst. Catalyst charges and feeds were introduced in the quantities and rates prescribed in Table II above.

It is believed that intermediate-surface-area supports at least initially have sufficient binding sites to retain the catalytic salts at a level sufficient for good performance and that reactor corrosion is related to the loss of catalyst salts from the catalyst as surface area is lost in the course of the oxychlorination process. Because of this, the maintenance of surface area of intermediate-surface area supports by means of inclusion of a Lanthanide Oxide in the support in accordance with this invention will make a particularly valuable contribution to significantly reduced reactor corrosion and overall process economy over the long term.

Some of the catalysts tested above were prepared using alumina supports possessing an initial surface area in excess of 160 $m^2/g$ while others were prepared using alumina supports possessing an initial surface area well below 100 $m^2/g$, see Table I. A similar beneficial effect of Lanthanide incorporation on the thermochemical stability of the catalyst compositions in high-temperature oxychlorination or calcination processes was qualitatively demonstrated in every test largely independent of the support surface area. However the use of a Lanthanide Oxide-modified support having an initial surface area below 100 $m^2/g$, i.e., 20 to 80 $m^2/g$, or more particularly from 35 to about 60 $m^2/g$, is preferred because of the favorable effect that support surface areas in this intermediate range exert on maintaining good HCl conversion while simultaneously minimizing reactor metal corrosion. Results in Table V show the advantage of using a catalyst based on a Lanthanide Oxide-modified alumina support having a surface area within the preferred range of 35 to about 60 $m^2/g$. Catalysts using Alumina E (Table I) having a surface area of 47 $m^2/g$ and Alumina F having a surface area of 92 $m^2/g$ (Table I) were tested in a 3.8-cm diameter reactor under conditions as described in Table II.

The catalyst based on Alumina E, which contained 4.9 percent Lanthanide Oxide, produced a significantly improved HCl conversion of 91 percent versus 76.9 percent for the catalyst based on Alumina F, which had a substantially higher initial surface area and contained 2.5 percent of Lanthanide Oxide. The catalyst efficiency of the catalyst based on Alumina E also is very significantly better than that of the catalyst based on Alumina F. The results are shown in Table V.

TABLE V

Effect of Catalyst Support Surface Area on Performance

Pressure Reactor (3.8 cm I.D.)
HCl/EDC = 1.2, HCl/Oxygen = 0.95

| Performance: | Catalyst Based on: | |
| --- | --- | --- |
| | Alumina E | Alumina F |
| Support Surface Area, $m^2/g$ | 47 | 92 |
| Temperature, °C. | 410 | 411 |
| Pressure, atm. | 4.1 | 4.1 |
| Bed Height, cm | 114 | 114 |
| S.L.V.d, cm/sec[a] | 8.5 | 8.5 |
| Residence time, sec | 13.3 | 13 |
| Catalyst Performance | | |
| HCl Conversion, % | 91.1 | 76.9 |
| Burning, % | 9.1 | 10.1 |
| PCE1 + TCE Selectivity, % | 69.6 | 68.6 |
| Efficiency[b] | 151.6 | 135.4 |

[a] Superficial Linear Velocity
[b] Efficiency = HCl conversion + (Perc + TCE) Selectivity − Burning (carbon oxides), all values as percent.

USE OF MAGNESIUM CHLORIDE

According to yet another and particularly preferred refinement of the invention an improved catalyst of the general type described above is provided which is especially effective in producing a relatively high proportion of either perchloroethylene or trichloroethylene as a matter of choice, with low burning losses and with accompanying increases in the total efficiency of the reaction under the conditions best suited for producing either product.

The process of making perchloroethylene and trichloroethylene by catalytic oxychlorination of $C_2$ Hydrocarbons is an especially complex one. In addition to the requirement for a catalyst and for reaction conditions favoring chlorination of the organic feed at a rapid rate, the chlorinated intermediates produced must be dehydrochlorinated at a rapid rate to allow further chlorination. With all of this, different catalysts as well as different reaction conditions are usually required depending on whether the production of perchloroethylene or of trichloroethylene is to be optimized. Processes for oxychlorinating $C_2$ Hydrocarbons commonly destroy a substantial though variable proportion of the organic feed through its conversion to carbon oxides. Trichloroethylene production is especially sensitive to high burning rates and requires care in the choice of catalyst and conditions.

In searching for compounds that would stabilize alumina supports against loss of surface area in the high-temperature environment of the oxychlorination reaction used to make perchloroethylene and trichloroethylene, it has now been unexpectedly found as part of this investigation that addition of a proper proportion of magnesium chloride, or other magnesium compound such as magnesium nitrate or magnesium acetate, to a catalyst composition possessing the characteristics described earlier herein gives improved performance in the form of reduced burning and usually also produces other improvements in terms of increased hydrogen chloride or chlorine conversion and higher selectivity to perchloroethylene and trichloroethylene. The improvement in performance has been found to be especially marked with feed ratios appropriate for the production of trichloroethylene.

The catalyst according to this embodiment of the invention is composed of copper(II) chloride, potassium chloride and magnesium chloride on supports consisting essentially of at least 90% alumina and at least 0.25 percent, and preferably 0.5 to 10 percent, of a Lanthanide Oxide. As described earlier herein, the weight ratio of potassium chloride to magnesium chloride is in the range from 0.5 1 to 3.0:1 in its preferred embodiment and is most preferably within the range of to 0.5:1 to 2.0:1. The salt ratio chosen is dependent on the ratio of perchloroethylene and trichloroethylene product desired. This salt ratio does not vary significantly with the surface area of the support.

Catalysts based on Lanthanide oxide-stabilized Alumina D, Table I, were prepared either with magnesium chloride (catalyst "G", Table VI), or without magnesium chloride (catalyst "H", Table VI). To further demonstrate the advantages of using magnesium chloride, similar catalysts, with and without magnesium chloride, "I and J" respectively in Table VI, were prepared using a silica-stabilized alumina support containing 1.6 percent silica and having a surface area of 35 m$^2$/g.

TABLE VI

Catalyst Compositions

| Catalyst | Support | Stabilizer, % | Salt Loading, Weight Percent | | |
|---|---|---|---|---|---|
| | | | CuCl2 | KCl | MgCl2 |
| G | Alumina D | Lanthanide Oxide, 4.6% | 9.42 | 4.42 | 4.42 |
| H | Alumina D | Lanthanide Oxide, 4.6% | 9.42 | 4.42 | — |
| I | | Silica, 1.6% | 8.65 | 3.65 | 3.65 |
| J | | Silica, 1.6% | 8.65 | 3.65 | — |

The following examples illustrates the effectiveness of this kind of oxychlorination catalyst when using ethylene dichloride as the organic feed in the production of perchloroethylene and trichloroethylene. However, the improvement is just as significant when ethane, ethylene or a partially chlorinated derivative thereof is used as feed.

As stated earlier, further improvement in catalyst performance is obtained when magnesium is included in the CuCl2/KCl catalyst composition used where making perchloroethylene and trichloroethylene by oxychlorination of hydrocarbons. In testing such catalyst compositions, oxychlorination runs were conducted using the 3.8-cm diameter pressurized fluidized-bed reactor described earlier in the example. The results shown in Tables VII and VIII point up the advantages obtained when the magnesium chloride-containing catalysts G and I, Table VI, were used. The use of these MgCl2-containing catalysts produced significant increases in HCl conversion, efficiency and selectivity as well as a significant reduction in burning of feed as compared with the results obtained when the catalysts made without any MgCl2 addition were used.

TABLE VII

Comparison of Catalysts G and H
In 3.8-cm Reactor Tests
(Lanthanide Oxide-Stabilized Alumina)

| Catalyst | G | H |
|---|---|---|
| MgCl2 | 4.42% | None |
| Feed Ratio (Molar) | | |
| HCl/EDC | 1.20 | 1.20 |
| HCl/Oxygen | 0.95 | 0.95 |
| Catalyst Performance: | | |
| HCl Conversion, % | 92.7 | 83.7 |
| Burning, % | 10.0 | 11.7 |
| PCE + TCE Selectivity | 68.8 | 65.0 |
| Efficiency$^a$ | 151.5 | 137.0 |

$^a$Efficiency = HCl Conversion + (Perc + TCE) Selectivity − Burning, all values as percent

TABLE VIII

Comparison of Catalysts I and J
In 5.1-cm Reactor Tests
(Silica-Stabilized Alumina)

| Catalyst | I | J |
|---|---|---|
| MgCl2 | 3.65% | None |
| Feed Ratio: Molar | | |
| HCl/EDC | 1.19 | 1.21 |
| HCl/Oxygen | 0.96 | 0.95 |
| Catalyst Performance: | | |
| HCl Conversion, % | 78.9 | 72.7 |
| Burning, % | 11.5 | 15.2 |
| PCE + TCE Selectivity | 66.5 | 67.6 |
| Efficiency$^a$ | 133.9 | 125.1 |

$^a$Efficiency = HCl Conversion + (Perc + TCE) Selectivity − Burning, all values as percent While the series of tests summarized in Table VII is not directly comparable with the series of tests summarized in Table VIII, both series show the beneficial effect of the presence of magnesium chloride in the catalyst. A comparison between the two series points to the fact that catalysts based on Lanthanide Oxide-stabilized alumina perform substantially better than similar catalysts based on silica-stabilized alumina.

EFFECT OF SALT RATIOS ON CATALYST PERFORMANCE

EXAMPLE 9

Use of Salt Ratios To Adjust Product Selectivity

Another new and unexpected advantage of the invention is the ability to provide flexibility in selectively producing either a high perchloroethylene yield or nearly equal amounts of perchloroethylene and trichloroethylene from the C2 Hydrocarbon feed. The desired product split is accomplished by adjustment of the cupric chloride, potassium chloride and magnesium chloride salt ratios in the catalyst. Four catalysts were prepared using Lanthanide Oxide-stabilized Alumina E (see Table I) having a wide range of weight ratios of cupric chloride to potassium chloride and of potassium chloride to magnesium chloride, as shown in Table IX-A. The catalyst formulations were tested in the 3.8-cm Inconel pressure reactor described in Example 7 with the catalyst charge and feeds conditions (which were held constant) as described in Table II. Performance test results are shown in Table IX-B.

Enhanced selectivity to perchloroethylene is achieved by using a cupric chloride to potassium chloride ratio of 4.0 to 6.0, with a ratio of about 5.0 being preferred. When using the relatively high cupric chloride to potassium chloride ratio of 5/1, it is best to use a low potassium chloride to magnesium chloride ratio in the range of 0.2 to 0.5, as shown in catalyst composition E-2, in order to reduce carbon burning losses and maintain high HCl conversions and good selectivity to perchloroethylene.

When relatively high selectivity to trichloroethylene is desired, optimum cupric chloride to potassium chloride and potassium chloride to magnesium chloride ratios are considerably different from those used for increasing selectivity to perchloroethylene. Relatively high selectivity to trichloroethylene is obtained using catalyst formulations containing cupric chloride to potassium chloride weight ratios of 0.5 to 2.0, with a ratio of 1.0 being preferred, plus potassium chloride to magnesium chloride weight ratios of 1.0 to 3.0, with a ratio of 2.0 preferred, as in catalyst E-4. Catalysts E-1 and E-3 lead to results intermediate to those obtained with catalysts E-2 and E-4, respectively.

TABLE IX-A

|  | Catalyst Compositions | | | |
| Catalyst | E-1 | E-2 | E-3 | E-4 |
| --- | --- | --- | --- | --- |
| Salt, Weight % | | | | |
| $CuCl_2$ | 9.1 | 8.0 | 11.2 | 6.4 |
| KCl | 4.1 | 1.6 | 3.2 | 6.4 |
| $MgCl_2$ | 4.1 | 6.4 | 1.6 | 3.2 |
| Weight Ratios | | | | |
| $CuCl_2$/KCl | 2.22 | 5.0 | 3.5 | 1.00 |
| KCl/$MgCl_2$ | 1.0 | 0.25 | 2.0 | 2.0 |
| $CuCl_2$/KCl + $MgCl_2$ | 1.11 | 1.0 | 2.33 | 0.68 |

TABLE IX-B

|  | Performance of Catalysts Compositions Tested In The 3.8-cm Reactor | | | |
| Catalyst | E-1 | E-2 | E-3 | E-4 |
| --- | --- | --- | --- | --- |
| Feed ratios, molar | | | | |
| HCl/Ethylene dichloride | 1.2 | 1.2 | 1.2 | 1.2 |
| HCl/oxygen | 0.84 | 0.84 | 0.84 | 0.84 |
| Catalyst Performance: | | | | |
| HCl Conversion, % | 92 | 90 | 89 | 90 |
| Burning, % | 14 | 14 | 17 | 15 |
| PCE + TCE Selectivity, % | 72 | 72 | 70 | 72 |
| PCE/TCE molar ratio | 1.3 | 2.3 | 1.8 | 0.9 |

In reading this specification and claims, it should always be understood that all quantities, ratio and percentages of materials are expressed on a weight basis unless some other basis is indicated explicitly or implicitly.

It should also be understood that while the foregoing description of the invention includes preferred embodiments and specific working examples, variations and modifications of what has been described may be employed by those skilled in the art without departing from the scope or spirit of this invention. Such variations and modifications are to be considered within the scope of the appended claims.

What is claimed is:

1. In a process for the production of at least one chlorinated hydrocarbon product selected from the group consisting of trichloroethylene and perchloroethylene by catalytic oxychlorination of a feedstock comprising a $C_2$ Hydrocarbon containing at least one less chlorine atom than the desired product, the catalytic oxychlorination being conducted in contact with a fluidized bed of particles of a copper chloride-containing catalyst composition in a reaction zone maintained at a temperature between 250° and 470° C. and at a pressure between 1 and 10 atmospheres, the improvement which comprises using as the catalyst a composition comprising copper chloride and alkali metal chloride deposited in catalytically active amounts on microspheroidal particles of a support which has a surface area in excess of 20 and less than 100 m²/g and comprises at least 90% alumina having from 0.2 to 10% of a Lanthanide Oxide selected from the group consisting of the oxides of lanthanum, enodymium, praseodymium and yttrium and mixtures comprising at least two of said Lanthanide oxides, intrinsically incorporated therein by heat treatment of the alumina at a temperature of at least 800° C. and up to 1500° C. after incorporation of a salt of the Lanthanide in the alumina.

2. A process according to claim 1, wherein the alumina in the support contains principally gamma-alumina, wherein the alkali metal chloride is potassium chloride and wherein the ratio of copper chloride to potassium chloride in the catalyst is between 0.8:1 and 5.0:1.

3. A process according to claim 1, wherein the reaction zone is maintained at a temperature between 380° and 450° C., and the catalyst is present therein in the form of a fluidized bed of microspheroidal particles.

4. In a process for the production of trichloroethylene and perchloroethylene by catalytic oxychlorination of a feedstock comprising a $C_2$ Hydrocarbon containing at least one less chlorine atom than the desired product, the catalytic oxychlorination being conducted in contact with a fluidized bed of particles of catalyst in a reaction zone maintained at a temperature between 380° C. and 450° C. and at a pressure between 1 and 10 atmospheres, the improvement which comprises using as the catalyst a composition comprising copper chloride and alkali metal chloride deposited in catalytically active amounts on microspheroidal particles of an alumina support which has a surface area between about 25 and 60 m2/g and which contains at least 90% alumina and from 0.5 to 5.0 percent of a Lanthanide Oxide selected from the group consisting of the oxides of lanthanum, neodymium, praseodymium and yttrium and mixtures comprising at least two of said Lanthanide Oxides, said Lanthanide Oxide being intrinsically incorporated in said alumina support by calcining said support at a temperature of at least 800° C. and up to 1500° C. after impregnation with a salt of said Lanthanide.

5. A process according to claim 4, wherein the Lanthanide Oxide in the alumina support comprises the oxide of lanthanum which is intrinsically incorporated in the alumina by calcining said support at a temperature of about 1200° C. after impregnation with a salt of lanthanum.

6. A process according to claim 4, wherein the catalyst comprises magnesium chloride in addition to copper chloride and potassium chloride, said magnesium chloride being present in a ratio equal to one weight of $MgCl_2$ per between 0.5 and 3.0 weights of KCl.

* * * * *